(12) United States Patent
Nielsen et al.

(10) Patent No.: US 10,308,899 B2
(45) Date of Patent: *Jun. 4, 2019

(54) LIQUID AUTOMATIC DISH WASHING DETERGENT COMPOSITIONS

(71) Applicant: Novozymes A/S, Bagsvaerd (DK)

(72) Inventors: Hanne Philbert Nielsen, Lyngby (DK); Lise Munch Mikkelsen, Roedovre (DK); Martin Noerby, Skovlunde (DK); Juan Jiang, Bagsvaerd (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/786,384

(22) PCT Filed: Apr. 23, 2014

(86) PCT No.: PCT/EP2014/058281
§ 371 (c)(1),
(2) Date: Oct. 22, 2015

(87) PCT Pub. No.: WO2014/173980
PCT Pub. Date: Oct. 30, 2014

(65) Prior Publication Data
US 2016/0068788 A1 Mar. 10, 2016

(30) Foreign Application Priority Data
Apr. 23, 2013 (EP) .................... 13164886

(51) Int. Cl.
| | |
|---|---|
| *C11D 3/386* | (2006.01) |
| *C07K 5/062* | (2006.01) |
| *C07K 5/087* | (2006.01) |
| *C07K 5/072* | (2006.01) |
| *C07K 5/083* | (2006.01) |
| *C07K 5/09* | (2006.01) |

(52) U.S. Cl.
CPC ...... *C11D 3/38663* (2013.01); *C11D 3/38618* (2013.01); *C07K 5/06026* (2013.01); *C07K 5/06043* (2013.01); *C07K 5/06052* (2013.01); *C07K 5/06095* (2013.01); *C07K 5/0806* (2013.01); *C07K 5/0808* (2013.01); *C07K 5/0812* (2013.01); *C07K 5/0817* (2013.01)

(58) Field of Classification Search
None
See application file for complete search history.

(56) References Cited

U.S. PATENT DOCUMENTS

| | | | |
|---|---|---|---|
| 6,143,707 A * | 11/2000 | Trinh | C11D 3/3907 134/25.2 |
| 2006/0035807 A1* | 2/2006 | Kasturi | A61K 8/44 510/475 |
| 2009/0215663 A1 | 8/2009 | Minning | |
| 2012/0003718 A1 | 1/2012 | Cascao-Pereira et al. | |
| 2012/0238005 A1 | 9/2012 | Wieland | |

FOREIGN PATENT DOCUMENTS

| | | |
|---|---|---|
| WO | 1994/04651 A1 | 3/1994 |
| WO | 1994/29428 A1 | 12/1994 |
| WO | 1998/13459 A1 | 4/1998 |
| WO | 2009/118375 A1 | 4/1998 |
| WO | 2011/036153 A1 | 3/2011 |
| WO | 2013/004636 A1 | 1/2013 |
| WO | 2013/188344 A2 | 12/2013 |

OTHER PUBLICATIONS

Ganz et al, 2004, Protein Engineering, Design and Selection, vol. 17, No. 4, pp. 333-339.
Li et al, 2003, Oil and chemical equipment cleaning technology, pp. 246-247, 251-252, 254-255.
Wang et al, 2000, Microbiology Bulletin, vol. 27, No. 3, pp. 218-220.

* cited by examiner

*Primary Examiner* — Michelle F. Paguio Frising
(74) *Attorney, Agent, or Firm* — Joshua Price

(57) ABSTRACT

The stabilization of subtilisins by peptide aldehydes, hydrosulfite adducts thereof or peptide methyl ketones, is particularly effective in liquid ADW detergents which contain a strong sequestering builder.

20 Claims, No Drawings
Specification includes a Sequence Listing.

SEQUENCE LISTING

<160> NUMBER OF SEQ ID NOS: 4

<210> SEQ ID NO 1
<211> LENGTH: 269
<212> TYPE: PRT
<213> ORGANISM: Bacillus lentus

<400> SEQUENCE: 1

```
Ala Gln Ser Val Pro Trp Gly Ile Ser Arg Val Gln Ala Pro Ala Ala
1               5                   10                  15
His Asn Arg Gly Leu Thr Gly Ser Gly Val Lys Val Ala Val Leu Asp
            20                  25                  30
Thr Gly Ile Ser Thr His Pro Asp Leu Asn Ile Arg Gly Gly Ala Ser
        35                  40                  45
Phe Val Pro Gly Glu Pro Ser Thr Gln Asp Gly Asn Gly His Gly Thr
50                  55                  60
His Val Ala Gly Thr Ile Ala Ala Leu Asn Asn Ser Ile Gly Val Leu
65                  70                  75                  80
Gly Val Ala Pro Ser Ala Glu Leu Tyr Ala Val Lys Val Leu Gly Ala
                85                  90                  95
Ser Gly Ser Gly Ser Val Ser Ser Ile Ala Gln Gly Leu Glu Trp Ala
            100                 105                 110
Gly Asn Asn Gly Met His Val Ala Asn Leu Ser Leu Gly Ser Pro Ser
        115                 120                 125
Pro Ser Ala Thr Leu Glu Gln Ala Val Asn Ser Ala Thr Ser Arg Gly
130                 135                 140
Val Leu Val Val Ala Ala Ser Gly Asn Ser Gly Ala Gly Ser Ile Ser
145                 150                 155                 160
Tyr Pro Ala Arg Tyr Ala Asn Ala Met Ala Val Gly Ala Thr Asp Gln
                165                 170                 175
Asn Asn Asn Arg Ala Ser Phe Ser Gln Tyr Gly Ala Gly Leu Asp Ile
            180                 185                 190
Val Ala Pro Gly Val Asn Val Gln Ser Thr Tyr Pro Gly Ser Thr Tyr
        195                 200                 205
Ala Ser Leu Asn Gly Thr Ser Met Ala Thr Pro His Val Ala Gly Ala
210                 215                 220
Ala Ala Leu Val Lys Gln Lys Asn Pro Ser Trp Ser Asn Val Gln Ile
225                 230                 235                 240
Arg Asn His Leu Lys Asn Thr Ala Thr Ser Leu Gly Ser Thr Asn Leu
                245                 250                 255
Tyr Gly Ser Gly Leu Val Asn Ala Glu Ala Ala Thr Arg
            260                 265
```

<210> SEQ ID NO 2
<211> LENGTH: 270
<212> TYPE: PRT
<213> ORGANISM: Artificial sequence
<220> FEATURE:
<223> OTHER INFORMATION: variant of SEQ ID NO: 1

<400> SEQUENCE: 2

```
Ala Gln Ser Val Pro Trp Gly Ile Ser Arg Val Gln Ala Pro Ala Ala
1               5                   10                  15
His Asn Arg Gly Leu Thr Gly Ser Gly Val Lys Val Ala Val Leu Asp
            20                  25                  30
Thr Gly Ile Ser Thr His Pro Asp Leu Asn Ile Arg Gly Gly Ala Ser
        35                  40                  45
Phe Val Pro Gly Glu Pro Ser Thr Gln Asp Gly Asn Gly His Gly Thr
50                  55                  60
His Val Ala Gly Thr Ile Ala Ala Leu Asn Asn Ser Ile Gly Val Leu
65                  70                  75                  80
```

```
Gly Val Ala Pro Ser Ala Glu Leu Tyr Ala Val Lys Val Leu Gly Ala
                85                  90                  95

Ala Asp Gly Ser Gly Ser Val Ser Ser Ile Ala Gln Gly Leu Glu Trp
            100                 105                 110

Ala Gly Asn Asn Gly Met His Val Ala Asn Leu Ser Leu Gly Ser Pro
        115                 120                 125

Ser Pro Ser Ala Thr Leu Glu Gln Ala Val Asn Ser Ala Thr Ser Arg
    130                 135                 140

Gly Val Leu Val Val Ala Ser Gly Asn Ser Gly Ala Gly Ser Ile
145                 150                 155                 160

Ser Tyr Pro Ala Arg Tyr Ala Asn Ala Met Ala Val Gly Ala Thr Asp
                165                 170                 175

Gln Asn Asn Asn Arg Ala Ser Phe Ser Gln Tyr Gly Ala Gly Leu Asp
            180                 185                 190

Ile Val Ala Pro Gly Val Asn Val Gln Ser Thr Tyr Pro Gly Ser Thr
        195                 200                 205

Tyr Ala Ser Leu Asn Gly Thr Ser Met Ala Thr Pro His Val Ala Gly
    210                 215                 220

Ala Ala Ala Leu Val Lys Gln Lys Asn Pro Ser Trp Ser Asn Val Gln
225                 230                 235                 240

Ile Arg Asn His Leu Lys Asn Thr Ala Thr Ser Leu Gly Ser Thr Asn
                245                 250                 255

Leu Tyr Gly Ser Gly Leu Val Asn Ala Glu Ala Ala Thr Arg
            260                 265                 270

<210> SEQ ID NO 3
<211> LENGTH: 270
<212> TYPE: PRT
<213> ORGANISM: Artificial sequence
<220> FEATURE:
<223> OTHER INFORMATION: variant of SEQ ID NO: 1

<400> SEQUENCE: 3

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Glu Gly Ser Gly Ser Val Ser Ser Ile Ala Gln Gly Leu Glu Trp
            100                 105                 110

Ala Gly Asn Asn Gly Met His Val Ala Asn Leu Ser Leu Gly Ser Pro
        115                 120                 125

Ser Pro Ser Ala Thr Leu Glu Gln Ala Val Asn Ser Ala Thr Ser Arg
    130                 135                 140

Gly Val Leu Val Val Ala Ala Ser Gly Asn Ser Gly Ala Gly Ser Ile
145                 150                 155                 160

Ser Tyr Pro Ala Arg Tyr Ala Asn Ala Met Ala Val Gly Ala Thr Asp
                165                 170                 175
```

Gln Asn Asn Asn Arg Ala Ser Phe Ser Gln Tyr Gly Ala Gly Leu Asp
            180                 185                 190

Ile Val Ala Pro Gly Val Asn Val Gln Ser Thr Tyr Pro Gly Ser Thr
        195                 200                 205

Tyr Ala Ser Leu Asn Gly Thr Ser Met Ala Thr Pro His Val Ala Gly
        210                 215                 220

Ala Ala Ala Leu Val Lys Gln Lys Asn Pro Ser Trp Ser Asn Val Gln
225                 230                 235                 240

Ile Arg Asn His Leu Lys Asn Thr Ala Thr Ser Leu Gly Ser Thr Asn
            245                 250                 255

Leu Tyr Gly Ser Gly Leu Val Asn Ala Glu Ala Thr Arg
        260                 265                 270

<210> SEQ ID NO 4
<211> LENGTH: 275
<212> TYPE: PRT
<213> ORGANISM: Artificial sequence
<220> FEATURE:
<223> OTHER INFORMATION: BPN' variant

<400> SEQUENCE: 4

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
130                 135                 140

Ser Gly Val Val Val Ala Ala Ala Gly Asn Glu Gly Thr Ser Gly Ser
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Leu Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

```
Leu Gly Asp Ser Phe Tyr Tyr Gly Lys Gly Leu Ile Asn Val Gln Ala
            260                 265                 270
Ala Ala Gln
    275
```

LIQUID AUTOMATIC DISH WASHING DETERGENT COMPOSITIONS

CROSS-REFERENCE TO RELATED APPLICATIONS

This application is a 35 U.S.C. 371 national application of PCT/EP2014/058281 filed Apr. 23, 2014 which claims priority or the benefit under 35 U.S.C. 119 of European application no. 13164886.7 filed Apr. 23, 2013 the contents of which are fully incorporated herein by reference.

REFERENCE TO A SEQUENCE LISTING

This application contains a Sequence Listing in computer readable form. The computer readable form is incorporated herein by reference.

FIELD OF THE INVENTION

The present invention relates to the stabilization of a subtilisin in a liquid automatic dish washing (ADW) detergent.

BACKGROUND

Liquid automatic dish washing (ADW) detergents are generally formulated with a content of builders. The formulation may include strong sequestering builders (e.g., phosphorus-containing builders such as phosphates and phosphonates), and it may also include other builders (e.g. weak or precipitating builders such as sodium carbonate, sodium bicarbonate and sodium citrate). Liquid ADW detergents are typically formulated without any anionic surfactant, but they may or may not contain a non-ionic surfactant.

When formulating a liquid dish washing (ADW) detergent, it is desirable to include a subtilisin-type protease in order to improve the removal of protein soiling. However, the storage stability of the subtilisin in the detergent can be a problem.

WO 94/29428 discloses liquid ADW detergents containing an enzyme and an enzyme stabilizing system which are free of phosphorus-containing builders. WO 94/04651 and WO 2009/118375 disclose liquid detergents comprising a protease and a peptide aldehyde as a reversible protease inhibitor.

SUMMARY

The inventors have found that the incorporation of a strong sequestering builder into a liquid ADW detergent tends to destabilize any subtilisin present, but that the incorporation of a peptide aldehyde is particularly effective for the stabilization of subtilisins in liquid ADW detergents which contain a strong sequestering builder.

Accordingly, the invention provides a liquid (dish wash detergent) composition comprising:
a) a strong sequestering builder,
b) a subtilisin, and
c) a subtilisin inhibitor which is a peptide aldehyde or a hydrosulfite adduct thereof or a peptide methyl ketone, wherein the methyl group is optionally halogen-substituted, and wherein the peptide optionally has an N-terminal protection group;
wherein the composition is essentially devoid of an anionic surfactant.

Other aspects and embodiments of the invention are apparent from the description and examples.

DETAILED DESCRIPTION

Subtilisin

In the context of the present invention, the Subtilisin family (EC 3.4.21.62) shall be understood as described by Siezen et al., *Protein Engng.* 4 (1991) 719-737 and Siezen et al. *Protein Science* 6 (1997) 501-523. As described therein, the Subtilisin family may be divided into 3 subgroups, i.e. I-S1 ("true" subtilisins), I-S2 (highly alkaline proteases) and intracellular subtilisins.

Examples of subtilisins are those derived from *Bacillus* such as subtilisin *lentus, Bacillus lentus*, subtilisin Novo, subtilisin Carlsberg, *Bacillus licheniformis*, subtilisin BPN', subtilisin 309, subtilisin 147 and subtilisin 168 described in WO 89/06279 and protease PD138 (WO 93/18140). Additional examples are described in WO 98/020115, WO 01/44452, WO 01/58275, WO 01/58276, WO 03/006602 and WO 04/099401.

Examples of useful variants are described in WO 92/19729, WO 98/20115, WO 98/20116, and WO 98/34946, especially the variants with substitutions in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using the BPN' numbering. More preferred the subtilase variants may comprise the mutations: S3T, V41, S9R, A15T, K27R, *36D, V68A, N76D, N87S,R, *97E, A98S, S99G,D,A, S99AD, S101G,M,R S103A, V104I,Y,N, S106A, G118V,R, H120D,N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering).

Examples of commercially available subtilisins include Kannase™, Everlase™ Primase™, Duralase™, Esperase™, Alcalase™, Durazym™, Savinase™, Ovozyme™ Liquanase™, Coronase™, Polarzyme™, Pyrase™, and ClearLens™ Pro; Blaze™ (Novozymes NS). Other commercially available proteases include Ronozyme™ Pro, Maxatase™ Maxacal™, Maxapem™, Opticlean™, Properase™, Purafect™, Purafect Ox™, Purafact Prime™, Excellase™, FN2™, FN3™ and FN4™ (available from Dupont).

In an embodiment of the invention, the subtilisin is subtilisin 309 or subtilisin BPN', or a variant of any of these. Preferably, the amino acid sequence of the subtilisin has at least 70% sequence identity, preferably at least 75%, more preferably at least 80%, more preferably at least 85%, more preferably at least 90%, more preferably at least 95%, 96%, 97%, 98%, 99%, and most preferably 100% sequence identity to the amino acid sequence of SEQ ID NO: 1 or SEQ ID NO: 4. In an embodiment, the amino acid sequence of the subtilisin is SEQ ID NO: 1, SEQ ID NO: 2, SEQ ID NO: 3, or SEQ ID NO: 4.

In an embodiment, the number of amino acid substitutions, deletions and/or insertions introduced into the amino acid sequence of SEQ ID NO: 1 or SEQ ID NO: 4 is up to 10, e.g., 1, 2, 3, 4, 5, 6, 7, 8, 9, or 10; or up to 5, e.g., 1, 2, 3, 4, or 5. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for subtilisin activity to identify amino acid residues that are critical to the activity of the molecule. See also, Hilton et al., 1996, *J. Biol. Chem.* 271: 4699-4708. The active site of the subtilisin or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

The relatedness between two amino acid sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows: (Identical Residues×100)/(Length of Alignment–Total Number of Gaps in Alignment).

Optional Additional Enzyme

In addition to the subtilisin, the composition may optionally comprise of one or more additional detergent enzymes such as 5, 4, 3, 2 or 1 additional enzyme(s). The additional enzymes may include an additional protease, a lipase, a cutinase, an amylase, a carbohydrase, a cellulase, a pectinase, a pectate lyase, a mannanase, an arabinase, a galactanase, a xylanase, an oxidase, a perhydrolase, a laccase, a peroxidase, and/or a haloperoxidase. Preferably, the additional enzyme is an amylase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Lipase and Cutinase

Suitable lipases and cutinases include those of bacterial or fungal origin. Chemically modified or protein engineered mutants are included. Examples include lipase from *Thermomyces*, e.g., from *T. lanuginosus* (previously named *Humicola lanuginosa*) as described in EP 258068 and EP 305216, cutinase from *Humicola*, e.g. *H. insolens* as described in WO 96/13580, a *Pseudomonas* lipase, e.g., from *P. alcaligenes* or *P. pseudoalcaligenes* (EP 218272), *P. cepacia* (EP 331376), *P. stutzeri* (GB 1372034), *P. fluorescens*, *Pseudomonas* sp. strain SD 705 (WO 95/06720 and WO 96/27002), *P. wisconsinensis* (WO 96/12012), a *Bacillus* lipase, e.g., from *B. subtilis* (Dartois et al., *Biochemica et Biophysica Acta*, (1993), 1131, 253-360), *B. stearothermophilus* (JP 64/744992) or *B. pumilus* (WO 91/16422), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in WO 92/05249, WO 94/01541, EP 407225, EP 260105, WO 95/35381, WO 96/00292, WO 95/30744, WO 94/25578, WO 95/14783, WO 95/22615, WO 97/04079, WO 97/07202, WO 00/060063, WO 07/087508 and WO 09/109500.

Preferred commercially available lipase enzymes include Lipolase™, Lipolase Ultra™, and Lipex™; Lecitase™, Lipolex™; Lipoclean™, Lipoprime™ (Novozymes NS). Other commercially available lipases include Lumafast (Genencor Int Inc); Lipomax (Gist-Brocades/Genencor Int Inc) and *Bacillus* sp lipase from Solvay.

Carbohydrase

A carbohydrase is a general term for enzymes that cleave carbohydrates. In general carbohydrases are named after the substrates they act on, for example amylases act on amylase and cellulases act on cellulose. Many carbohydrases have found use in cleaning and laundry applications, such as amylase, cellulase, pectinase, pectate lyase, mannanase, arabinase, galactanase and xylanase, and all these can be applied in the liquid composition.

Amylase

Suitable amylases include those of bacterial or fungal origin. Chemically modified or protein engineered mutants are included. Amylases include, for example, α-amylases obtained from *Bacillus*, e.g., a special strain of *Bacillus licheniformis*, described in more detail in GB 1,296,839.

Examples of suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193. Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:
M197T;
H156Y+A181T+N190F+A209V+Q264S; or
G48A+T491+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476. More preferred variants are those having a deletion in positions 181 and 182 or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:
N128C+K178L+T182G+Y305R+G475K;
N128C+K178L+T182G+F202Y+Y305R+D319T+G475K;
S125A+N128C+K178L+T182G+Y305R+G475K; or
S125A+N128C+T131I+T165I+K178L+T182G+Y305R+G475K wherein the variants are C-terminally truncated and optionally further comprises a substitution at position 243 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particularly preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Stainzyme; Stainzyme Plus; Duramyl™, Termamyl™, Termamyl Ultra; Natalase, Fungamyl™ and BAN™ (Novozymes NS), Rapidase™ and Purastar™/Effectenz™, Powerase and Preferenz S100 (from Genencor International Inc./DuPont).

Lyases

The lyase may be a pectate lyase derived from *Bacillus*, particularly *B. lichemiformis* or *B. agaradhaerens*, or a variant derived of any of these, e.g. as described in U.S. Pat. No. 6,124,127, WO 99/027083, WO 99/027084, WO 02/006442, WO 02/092741, WO 03/095638, Commercially available pectate lyases are XPect; Pectawash and Pectaway (Novozymes NS).

Mannanase

The mannanase may be an alkaline mannanase of Family 5 or 26. It may be a wild-type from *Bacillus* or *Humicola*, particularly *B. agaradhaerens*, *B. licheniformis*, *B. halodurans*, *B. clausii*, or *H. insolens*. Suitable mannanases are described in WO 99/064619. A commercially available mannanase is Mannaway (Novozymes NS).

Cellulase

Suitable cellulases may be of bacterial or fungal origin. Chemically or genetically modified mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259. Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, US Commercially available cellulases include Carezyme™, Celluzyme™, Celluclean™ Celluclast™, and Endolase™; Renozyme; Whitezyme (Novozymes NS), Clazinase™ Puradax, Puradax HA, and Puradax EG (available from Genencor) and KAC-500(B)™ (Kao Corporation).

Peroxidases/Oxidases

Suitable peroxidases are comprised by the enzyme classification EC 1.11.1.7, as set out by the Nomenclature Committee of the International Union of Biochemistry and Molecular Biology (IUBMB), or any fragment derived therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257.

The peroxidases also include a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions.

In an embodiment, the haloperoxidase of the invention is a chloroperoxidase. Preferably, the haloperoxidase is a vanadium haloperoxidase, i.e., a vanadate-containing haloperoxidase. In a preferred method of the present invention the vanadate-containing haloperoxidase is combined with a source of chloride ion.

Haloperoxidases have been isolated from many different fungi, in particular from the fungus group dematiaceous hyphomycetes, such as *Caldariomyces*, e.g., *C. fumago*, *Alternaria*, *Curvularia*, e.g., *C. verruculosa* and *C. inaequalis*, *Drechslera*, *Ulocladium* and *Botrytis*.

Haloperoxidases have also been isolated from bacteria such as *Pseudomonas*, e.g., *P. pyrrocinia* and *Streptomyces*, e.g., *S. aureofaciens*.

In an preferred embodiment, the haloperoxidase is derivable from *Curvularia* sp., in particular *Curvularia verruculosa* or *Curvularia inaequalis*, such as *C. inaequalis* CBS 102.42 as described in WO 95/27046; or *C. verruculosa* CBS 147.63 or *C. verruculosa* CBS 444.70 as described in WO 97/04102; or from *Drechslera hartlebii* as described in WO 01/79459, *Dendryphiella salina* as described in WO 01/79458, *Phaeotrichoconis crotalarie* as described in WO 01/79461, or *Geniculosporium* sp. as described in WO 01/79460.

Suitable oxidases include, in particular, any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5).

Preferred laccase enzymes are enzymes of microbial origin. The enzymes may be derived from plants, bacteria or fungi (including filamentous fungi and yeasts).

Suitable examples from fungi include a laccase derivable from a strain of *Aspergillus*, *Neurospora*, e.g., *N. crassa*, *Podospora*, *Botrytis*, *Collybia*, *Fomes*, *Lentinus*, *Pleurotus*, *Trametes*, e.g., *T. villosa* and *T. versicolor*, *Rhizoctonia*, e.g., *R. solani*, *Coprinopsis*, e.g., *C. cinerea*, *C. comatus*, *C. friesii*, and *C. plicatilis*, *Psathyrella*, e.g., *P. condelleana*, *Panaeolus*, e.g., *P. papilionaceus*, *Myceliophthora*, e.g., *M. thermophila*, *Schytalidium*, e.g., *S. thermophilum*, *Polyporus*, e.g., *P. pinsitus*, *Phlebia*, e.g., *P. radiata* (WO 92/01046), or *Coriolus*, e.g., *C. hirsutus* (JP 2238885).

Suitable examples from bacteria include a laccase derivable from a strain of *Bacillus*. A laccase derived from *Coprinopsis* or *Myceliophthora* is preferred; in particular a laccase derived from *Coprinopsis cinerea*, as disclosed in WO 97/08325; or from *Myceliophthora thermophila*, as disclosed in WO 95/33836.

Perhydrolase

Suitable perhydrolases are capable of catalyzing a perhydrolysis reaction that results in the production of a peracid from a carboxylic acid ester (acyl) substrate in the presence of a source of peroxygen (e.g., hydrogen peroxide). While many enzymes perform this reaction at low levels, perhydrolases exhibit a high perhydrolysis:hydrolysis ratio, often greater than 1. Suitable perhydrolases may be of plant, bacterial or fungal origin. Chemically modified or protein engineered mutants are included.

Examples of useful perhydrolases include naturally occurring *Mycobacterium* perhydrolase enzymes, or variants thereof. An exemplary enzyme is derived from *Mycobacterium smegmatis*. Such enzyme, its enzymatic properties, its structure, and variants thereof, are described in WO 2005/056782, WO 2008/063400, US 2008/145353, and US2007167344.

Inhibitor

The inhibitor used in the liquid composition of the invention is a peptide aldehyde, a hydrosulfite adduct thereof, or a peptide methyl ketone. The methyl group is optionally halogen-substituted, and the peptide optionally has an N-terminal protection group.

Aldehyde or Ketone

The inhibitor may have the formula: P-(A)$_y$-L-(B)$_x$—B$^0$—R* wherein:

R* is H (hydrogen), CH$_3$, CX$_3$, CHX$_2$, or CH$_2$X. Preferably, R*=H so that the inhibitor is a peptide aldehyde with the formula P-(A)$_y$-L-(B)$_x$—B$^0$—H;

X is a halogen atom, particularly F (fluorine);

B$^0$ is a single amino acid residue with L- or D-configuration of the formula —NH—CH(R)—C(=O)—;

x is 1, 2 or 3;

B$_x$ is independently a single amino acid residue, each connected to the next B or to B$^0$ via its C-terminal;

L is absent or independently a linker group of the formula —C(=O)—, —C(=O)—C(=O)—, —C(=S)—, —C(=S)—C(=S)— or —C(=S)—C(=O)—;

A is absent if L is absent or is independently a single amino acid residue connected to L via the N-terminal of the amino acid;

P is selected from the group consisting of hydrogen or if L is absent an N-terminal protection group;

y is 0, 1, or 2,

R is independently selected from the group consisting of C$_{1-6}$ alkyl, C$_{6-10}$ aryl or C$_{7-10}$ arylalkyl optionally substituted with one or more, identical or different, substituent's R';

R' is independently selected from the group consisting of halogen, —OH, —OR", —SH, —SR", —NH$_2$, —NHR", —NR"$_2$, —CO$_2$H, —CONH$_2$, —CONHR", —CONR"$_2$, —NHC(=N)NH$_2$; and R" is a C$_{1-6}$ alkyl group.

x may be 1, 2 or 3 and therefore B may be 1, 2 or 3 amino acid residues respectively. Thus, B may represent B$^1$, B$^2$—B$^1$ or B$^3$—B$^2$—B$^1$, where B$^3$, B$^2$ and B$^1$ each represent one amino acid residue. y may be 0, 1 or 2 and therefore A may be absent, or 1 or 2 amino acid residues respectively having the formula $A^1$ or $A^2$-$A^1$ wherein $A^2$ and $A^1$ each represent one amino acid residue.

$B^0$ may be a single amino acid residue with L- or D-configuration, which is connected to H via the C-terminal of the amino acid. $B^0$ has the formula —NH—CH(R)—C(=O)—, wherein R is a $C_{1-6}$ alkyl, $C_{6-10}$ aryl or $C_{7-10}$ arylalkyl side chain, such as methyl, ethyl, propyl, isopropyl, butyl, isobutyl, phenyl or benzyl, and wherein R may be optionally substituted with one or more, identical or different, substituent's R'. Particular examples of $B^0$ are the D- or L-form of arginine (Arg), 3,4-dihydroxyphenylalanine, isoleucine (Ile), leucine (Leu), methionine (Met), norleucine (Nle), norvaline (Nva), phenylalanine (Phe), m-tyrosine, p-tyrosine (Tyr) and valine (Val). A particular embodiment is when $B^0$ is leucine, methionine, phenylalanine, p-tyrosine and valine.

$B^1$, which is connected to $B^0$ via the C-terminal of the amino acid, may be an aliphatic, hydrophobic and/or neutral amino acid. Examples of $B^1$ are alanine (Ala), cysteine (Cys), glycine (Gly), isoleucine (Ile), leucine (Leu), norleucine (Nle), norvaline (Nva), proline (Pro), serine (Ser), threonine (Thr) and valine (Val). Particular examples of $B^1$ are alanine, glycine, isoleucine, leucine and valine. A particular embodiment is when $B^1$ is alanine, glycine or valine.

If present, $B^2$, which is connected to $B^1$ via the C-terminal of the amino acid, may be an aliphatic, hydrophobic, neutral and/or polar amino acid. Examples of $B^2$ are alanine (Ala), arginine (Arg), capreomycidine (Cpd), cysteine (Cys), glycine (Gly), isoleucine (Ile), leucine (Leu), norleucine (Nle), norvaline (Nva), phenylalanine (Phe), proline (Pro), serine (Ser), threonine (Thr), and valine (Val). Particular examples of $B^2$ are alanine, arginine, capreomycidine, glycine, isoleucine, leucine, phenylalanine and valine. A particular embodiment is when $B^2$ is arginine, glycine, leucine, phenylalanine or valine.

$B^3$, which if present is connected to $B^2$ via the C-terminal of the amino acid, may be a large, aliphatic, aromatic, hydrophobic and/or neutral amino acid. Examples of $B^3$ are isoleucine (Ile), leucine (Leu), norleucine (Nle), norvaline (Nva), phenylalanine (Phe), phenylglycine, tyrosine (Tyr), tryptophan (Trp) and valine (Val). Particular examples of $B^3$ are leucine, phenylalanine, tyrosine and tryptophan.

The linker group L may be absent or selected from the group consisting of —C(=O)—, —C(=O)—C(=O)—, —C(=S)—, —C(=S)—C(=S)— or —C(=S)—C(=O)—. Particular embodiments of the invention are when L is absent or L is a carbonyl group —C(=O)—.

$A^1$, which if present is connected to L via the N-terminal of the amino acid, may be an aliphatic, aromatic, hydrophobic, neutral and/or polar amino acid. Examples of $A^1$ are alanine (Ala), arginine (Arg), capreomycidine (Cpd), glycine (Gly), isoleucine (Ile), leucine (Leu), norleucine (Nle), norvaline (Nva), phenylalanine (Phe), threonine (Thr), tyrosine (Tyr), tryptophan (Trp) and valine (Val). Particular examples of $A^1$ are alanine, arginine, glycine, leucine, phenylalanine, tyrosine, tryptophan and valine. A particular embodiment is when $B^2$ is leucine, phenylalanine, tyrosine or tryptophan.

The $A^2$ residue, which if present is connected to $A^1$ via the N-terminal of the amino acid, may be a large, aliphatic, aromatic, hydrophobic and/or neutral amino acid. Examples of $A^2$ are arginine (Arg), isoleucine (Ile), leucine (Leu), norleucine (Nle), norvaline (Nva), phenylalanine (Phe), phenylglycine, Tyrosine (Tyr), tryptophan (Trp) and valine (Val). Particular examples of $A^2$ are phenylalanine and tyrosine.

The N-terminal protection group P (if present) may be selected from formyl, acetyl (Ac), benzoyl (Bz), trifluoroacetyl, methoxysuccinyl, aromatic and aliphatic urethane protecting groups such as fluorenylmethyloxycarbonyl (Fmoc), methoxycarbonyl (Moc), (fluoromethoxy)carbonyl, benzyloxycarbonyl (Cbz), t-butyloxycarbonyl (Boc) and adamantyloxycarbonyl; p-methoxybenzyl carbonyl, benzyl (Bn), p-methoxybenzyl (PMB), p-methoxyphenyl (PMP), methoxyacetyl, methylamino carbonyl, methylsulfonyl, ethylsulfonyl, benzylsulfonyl, methylphosphoramidyl (MeOP(OH)(=O)) and benzylphosphoramidyl ($PhCH_2OP(OH)$(=O)).

In the case of a tripeptide aldehyde with a protection group (i.e. x=2, L is absent and A is absent), P is preferably acetyl, methoxycarbonyl, benzyloxycarbonyl, methylamino carbonyl, methylsulfonyl, benzylsulfonyl and benzylphosphoramidyl. In the case of a tetrapeptide aldehyde with a protection group (i.e. x=3, L is absent and A is absent), P is preferably acetyl, methoxycarbonyl, methylsulfonyl, ethylsulfonyl and methylphosphoramidyl.

Suitable peptide aldehydes are described in WO94/04651, WO95/25791, WO98/13458, WO98/13459, WO98/13460, WO98/13461, WO98/13462, WO07/141736, WO07/145963, WO09/118375, WO10/055052 and WO11/036153. More particularly, the peptide aldehyde may be Cbz-Arg-Ala-Tyr-H, Ac-Gly-Ala-Tyr-H, Cbz-Gly-Ala-Tyr-H, Cbz-Gly-Ala-Tyr-$CF_3$, Cbz-Gly-Ala-Leu-H, Cbz-Val-Ala-Leu-H, Cbz-Val-Ala-Leu-$CF_3$, Moc-Val-Ala-Leu-$CF_3$, Cbz-Gly-Ala-Phe-H, Cbz-Gly-Ala-Phe-$CF_3$, Cbz-Gly-Ala-Val-H, Cbz-Gly-Gly-Tyr-H, Cbz-Gly-Gly-Phe-H, Cbz-Arg-Val-Tyr-H, Cbz-Leu-Val-Tyr-H, Ac-Leu-Gly-Ala-Tyr-H, Ac-Phe-Gly-Ala-Tyr-H, Ac-Tyr-Gly-Ala-Tyr-H, Ac-Phe-Gly-Ala-Leu-H, Ac-Phe-Gly-Ala-Phe-H, Ac-Phe-Gly-Val-Tyr-H, Ac-Phe-Gly-Ala-Met-H, Ac-Trp-Leu-Val-Tyr-H, MeO—CO-Val-Ala-Leu-H, MeNCO-Val-Ala-Leu-H, MeO—CO-Phe-Gly-Ala-Leu-H, MeO—CO-Phe-Gly-Ala-Phe-H, $MeSO_2$-Phe-Gly-Ala-Leu-H, $MeSO_2$-Val-Ala-Leu-H, $PhCH_2O$—P(OH)(O)-Val-Ala-Leu-H, $EtSO_2$-Phe-Gly-Ala-Leu-H, $PhCH_2SO_2$—Val-Ala-Leu-H, $PhCH_2O$—P(OH)(O)-Leu-Ala-Leu-H, $PhCH_2O$—P(OH)(O)-Phe-Ala-Leu-H, or MeO—P(OH)(O)-Leu-Gly-Ala-Leu-H. A preferred inhibitor for use in the liquid composition of the invention is Cbz-Gly-Ala-Tyr-H, or a hydrosulfite adduct thereof, wherein Cbz is benzyloxycarbonyl.

Further examples of such peptide aldehydes include α-MAPI, β-MAPI, Phe-C(=O)-Arg-Val-Tyr-H, Phe-C(=O)-Gly-Gly-Tyr-H, Phe-C(=O)-Gly-Ala-Phe-H, Phe-C(=O)-Gly-Ala-Tyr-H, Phe-C(=O)-Gly-Ala-L-H, Phe-C(=O)-Gly-Ala-Nva-H, Phe-C(=O)-Gly-Ala-Nle-H, Tyr-C(=O)-Arg-Val-Tyr-H, Tyr-C(=O)-Gly-Ala-Tyr-H, Phe-C(=S)-Arg-Val-Phe-H, Phe-C(=S)-Arg-Val-Tyr-H, Phe-C(=S)-Gly-Ala-Tyr-H, Antipain, GE20372A, GE20372B, Chymostatin A, Chymostatin B, and Chymostatin C.

Hydrosulfite Adduct

The subtilisin inhibitor may be a hydrosulfite adduct of an aldehyde described above, e.g. as described in WO 2013/004636. The adduct may have the formula P-$(A)_y$L-$(B)_x$—N(H)—CHR—CH(OH)—$SO_3M$, wherein P, A, y, L, B, x and R are defined as above, and M is H or an alkali metal, preferably Na or K. A preferred embodiment is a hydrosulfite adduct wherein P=Cbz, $B^2$=Gly; $B^1$=Ala; $B^0$=Tyr (so R=$PhCH_2$, R'=OH), x=2, y=0, L=A=absent and M=Na.

Aldehyde or Hydrosulfite Adduct

The inhibitor may be an aldehyde having the formula P—$B^2$—$B^1$—$B^0$—H or an adduct having the formula P—$B^2$—$B^1$—N(H)—CHR—CHOH—$SO_3M$, wherein a) H is hydrogen;
b) $B^0$ is a single amino acid residue with L- or D-configuration of the formula —NH—CH(R)—C(=O)—;
c) $B^1$ and $B^2$ are independently single amino acid residues;
d) R is independently selected from the group consisting of $C_{1-6}$ alkyl, $C_{6-10}$ aryl or $C_{7-10}$ arylalkyl optionally substituted with one or more, identical or different, substituent's R';
e) R' is independently selected from the group consisting of halogen, —OH, —OR", —SH, —SR", —NH$_2$, —NHR", —NR"$_2$, —CO$_2$H, —CONH$_2$, —CONHR", —CONR"$_2$, —NHC(=N)NH$_2$;
f) R" is a $C_{1-6}$ alkyl group; and
g) P is an N-terminal protection group.
Constituents b) to g) may be selected as described above.

Strong Sequestering Builders

A sequestering builder is different from a precipitating builder in that no significant amount of precipitate is formed when the builder is used in an amount sufficient to combine with all of the calcium ions in an aqueous solution with 7° dH hardness (German hardness) initially at neutral pH.

A strong builder is classified as high efficiency chelators that can bind the divalent cations such as $Ca^{2+}$ strongly with a logarithmic stability constant (Log $K_{ca}$) of the cation/chelator complex of above 4, particularly above 5, above 6 or above 7. The stability constants are determined at an ionic strength of 0.1 M and at a temperature of 25° C.

For further details see, e.g., Arthur E. Martell and Robert M. Smith, Critical Stability Constants, Plenum Press, New York, 1975, vol. 1-6; or NIST Critically Selected Stability Constants of Metal Complexes at http://www.nist.gov/srd/nist46.cfm.

Strong sequestering builders include for example, such materials as water-soluble tripolyphosphate, ethylene diamine tetraacetate, and organic phosphonates. Alkali metal pyrophosphates are also classed as sequestering builders. The strong sequestering builder may be a phosphorus-containing builder or a non-phosphorus builder.

A phosphorus-containing builder generally comprises an inorganic phosphate or a phosphonate, typically an alkali metal salt such as sodium or potassium.

The inorganic phosphate may be a diphosphate, a triphosphate, a tripolyphosphate or pyrophosphate. Specific examples of inorganic phosphates include $Na_5P_3O_{10}$ (STPP or sodium tripolyphosphate) and $Na_4P_2O_7$ (tetrasodium pyrophosphate).

The phosphonate may be an alkyl phosphonate, an aryl phosphonate or an alkaryl phosphonate, wherein the alkyl, aryl or alkaryl group may be substituted. Examples of phosphonates include 1-Hydroxy Ethylidene-1,1-Diphosphonic Acid (HEDP, etidronic acid), Diethylenetriamine Penta(Methylene Phosphonic acid) (DTPMP), Ethylene diamine tetra(methylene phosphonic acid) (EDTMPA), amino tris(methylenephosphonic acid) (ATMP), Nitrilo trimethylene phosphonic acid (NTMP), 2-Amino ethyl phosphonic acid (AEPn), Dimethyl methylphosphonate (DMMP), Tetramethylene diamine tetra(methylene phosphonic acid) (TDTMP), Hexamethylene diamine tetra(methylene phosphonic acid) (HDTMP), Phosphonobutane-tricarboxylic acid (PBTC), N-(phosphonomethyl) iminodiacetic acid (PMIDA), 2-carboxyethyl phosphonic acid (CEPA), 2-Hydroxy phosphonocarboxylic acid (HPAA).

A non-phosphorus strong sequestering builder may include for example, Ethylenediaminetetraacetic acid (EDTA), methylglycinediacetic acid (MGDA), Nitrilotri-acetic acid (NTA), iminodisuccinic acid (IDS), ethylenediaminedisuccinic acid (EDDS), and L-glutamic acid N,N-diacetic acid tetra sodium salt (GLDA).

Examples of stability constants on the builder calcium complex are listed below:

TABLE 1

| Builder | Builder type | Phosphorus | Log $K_{Ca}$ |
|---|---|---|---|
| Strong sequestering builders | | | |
| EDTA | Sequestering | no | 10.7 |
| EDTMP | Sequestering | yes | 10.0 |
| NTMP | Sequestering | yes | 7.6 |
| DTPMP | Sequestering | yes | 7.1 |
| MGDA | Sequestering | no | 7 |
| NTA | Sequestering | no | 6.4 |
| HEDP | Sequestering | yes | 6 |
| STPP | Sequestering | yes | 5.36 |
| IDS | Sequestering | no | 5.2 |
| GLDA | Sequestering | no | 5.2 |
| Pyrophosphate | Sequestering | yes | 5 |
| EDDS | Sequestering | no | 4.6 |
| Other builders | | | |
| Carbonate | Precipitating | no | 7.8 |
| Citric acid | Sequestering | no | 3.5 |
| AMP | Sequestering | yes | 1.7 |

Other Optional Builders

In addition to the strong sequestering builder, the liquid composition may optionally comprise one or more other builders, e.g. a weak builder or a precipitating builder. Precipitating builders are materials such as carbonates, bicarbonates, sesquicarbonates, silicates, aluminates, oxylates, and fatty acids, particularly as an alkali metal salt such as sodium or potassium Examples of optional builders include sodium citrate, citric acid, alcanol amines such as Mono- di- or Triethanol amine (MEA, DEA or TEA), sodium carbonate (precipitating, log $K_{Ca}$=7.8), sodium bicarbonate and Amino-tris-(methylene-phosphonic acid) (AMP).

Surfactants

The liquid composition is essentially devoid of anionic surfactant, i.e. below 1% or below 0.5% by weight.

The liquid composition may be essentially devoid of any surfactant, or it may comprise non-ionic surfactants, typically in an amount below 5% by weight. Examples include block-copolymers based on ethyleneoxide and propylenoxide, such as Pluronic™ from BASF, fatty alcohol ethoxylate such as Lutensol™ from BASF, and Alcohol Alkoxylates such as Plurafac™ from BASF.

Other non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), methylester ethoxylates (MEE), as well as products available under the trade names SPAN and TWEEN, and combinations thereof.

Amounts

The subtilisin and the optional second enzyme may each be present in the liquid detergent in an amount in the range from 0.0001% (w/w) to 5% (w/w). Typical amounts are in the range from 0.01% to 2% by weight of the liquid detergent composition.

The molar ratio of the peptide aldehyde (or hydrosulfite adduct) to the protease may be at least 1:1 or 1.5:1, and it may be less than 1000:1, more preferred less than 500:1, even more preferred from 100:1 to 2:1 or from 20:1 to 2:1, or most preferred, the molar ratio is from 10:1 to 2:1.

The strong sequestering builder may be present in the liquid composition in an amount above 0.1% by weight, particularly above 0.3%, above 1%, above 5%, above 10%, above 15% or above 20%. The amount may be below 20%, below 15%, below 10, below 5% or below 2%.

The phosphorus-containing builder may be present in the liquid composition in an amount corresponding to a phosphorus content of at least 0.1% by weight of the composition, particularly above 1%, above 2%, above 3%, above 4% or above 5% by weight. The amount may correspond to a phosphorus content below 8%, particularly below 6%, below 2%, below 1% or below 0.5%.

Bleaching System

The liquid (dish wash detergent) composition may contain 0-30% by weight, such as about 1% to about 20%, of a bleaching system. Any bleaching system known in the art for use in laundry detergents may be utilized. Suitable bleaching system components include bleaching catalysts, photobleaches, bleach activators, sources of hydrogen peroxide such as sodium percarbonate, sodium perborates and hydrogen peroxide—urea (1:1), preformed peracids and mixtures thereof. Suitable preformed peracids include, but are not limited to, peroxycarboxylic acids and salts, diperoxydicarboxylic acids, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term bleach activator is meant herein as a compound which reacts with hydrogen peroxide to form a peracid via perhydrolysis. The peracid thus formed constitutes the activated bleach. Suitable bleach activators to be used herein include those belonging to the class of esters, amides, imides or anhydrides. Suitable examples are tetraacetylethylenediamine (TAED), sodium 4-[(3,5,5-trimethylhexanoyl)oxy]benzene-1-sulfonate (ISONOBS), 4-(dodecanoyloxy)benzene-1-sulfonate (LOBS), 4-(decanoyloxy) benzene-1-sulfonate, 4-(decanoyloxy)benzoate (DOBS or DOBA), 4-(nonanoyloxy)benzene-1-sulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like triacetin has the advantage that it is environmentally friendly Furthermore acetyl triethyl citrate and triacetin have good hydrolytical stability in the product upon storage and are efficient bleach activators. Finally ATC is multifunctional, as the citrate released in the perhydrolysis reaction may function as a builder. Alternatively, the bleaching system may comprise peroxyacids of, for example, the amide, imide, or sulfone type. The bleaching system may also comprise peracids such as 6-(phthalimido)peroxyhexanoic acid (PAP). The bleaching system may also include a bleach catalyst. In some embodiments the bleach component may be an organic catalyst selected from the group consisting of organic catalysts having the following formulae:

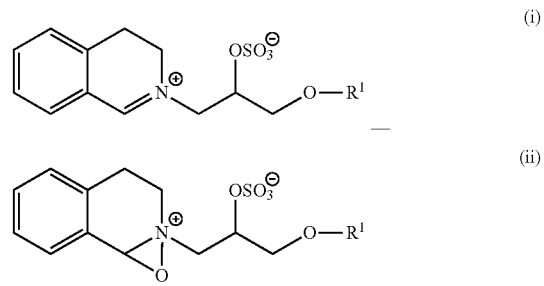

(iii) and mixtures thereof, wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl. Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

Preferably the bleach component comprises a source of peracid in addition to bleach catalyst, particularly organic bleach catalyst. The source of peracid may be selected from (a) pre-formed peracid; (b) percarbonate, perborate or persulfate salt (hydrogen peroxide source) preferably in combination with a bleach activator; and (c) perhydrolase enzyme and an ester for forming peracid in situ in the presence of water in a textile or hard surface treatment step.

Other Ingredients

For dissolution of the surfactant and other detergent ingredients, a solvent system is needed. Solvents are typically water, alcohols, polyols, sugars and/or mixtures thereof. Preferred solvents are water, glycerol, sorbitol, propylene glycol (MPG, 1,2-propanediol or 1,3-propane diol), dipropylene glycol (DPG), polyethylene glycol family (PEG300-600), hexylene glycol, inositol, mannitol, Ethanol, isopropanol, n-butoxy propoxy propanol, ethanolamines (monoethanol amine, diethanol amines and triethanol amines), sucrose, dextrose, glucose, ribose, xylose, and related mono and di pyranosides and furanosides.

The solvent system is present in typically totally 5-90%, 5-60%, 5-40%, 10-30% by weight. The water content for unit doses wrapped in PVA film is typically in the range 1-15%, 2-12%, 3-10%, 5-10%.

The polyol content for unit doses wrapped in PVA film is typically in the range 5-50%, 10-40% or 20-30%.

The liquid composition may comprise a thickener agent such as polyacrylate, polysaccharide or polysaccharide derivative type including pectine, alginate, arabinogalactan (gum Arabic), carrageenan, gellan gum, xanthan gum and guar gum, e.g. in an amount of 0.1% to about 10%, preferably from about 0.3% to about 8%, most preferably from about 0.5% to about 5%, by weight.

The liquid composition may also comprise a hydrotrope, which is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants), however the molecular structure of hydrotropes generally do not favor spontaneous self-aggregation, see e.g. review by Hodgdon and Kaler (2007), Current Opinion in Colloid & Interface Science 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity. The detergent may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Liquid Composition

The liquid composition of the invention has a physical form, which is not solid (or gas). It may be a pourable liquid, a pourable gel or a non-pourable gel. It may be either isotropic or structured, preferably isotropic. It may be a liquid detergent useful for washing in automatic washing machines.

In an embodiment, the invention is directed to liquid dish wash or ADW (Automatic Dish Wash) detergent compositions. The choice of additional detergent components is within the skill of the artisan and includes conventional ingredients, including the exemplary non-limiting components set forth above and below.

The liquid composition may be comprised in a unit dose product. A unit dose product is the packaging of a single dose in a non-reusable container. It is increasingly used in detergents for laundry and dish wash. A detergent unit dose product is the packaging (e.g., in a detergent pouch made from a water soluble film) of the amount of detergent used for a single wash.

A detergent pouch may be configured as single or multi compartments (see e.g., WO 2009/098660 or WO 2010/141301). It can be of any form, shape and material which is suitable for holding the detergent composition, e.g., without allowing release of the composition from the pouch prior to water contact. The pouch is made from water-soluble film which encloses the inner volume (detergent composition). Said inner volume can be divided into compartments of the pouch. The pouch can comprise a solid laundry cleaning (detergent) composition or selected components thereof, and/or a liquid cleaning composition or selected components thereof, separated by the water-soluble film. The pouch may include compartments having any combination of solids and liquids, both in one or more separate compartments, and in shared compartments containing both solid and liquid ingredients. The pouch may include regions or compartments formed by different water-soluble films, which can be with or without enzymes. Accordingly, detergent ingredients can be separated physically from each other in different compartments. Thereby negative storage interaction between components can be avoided. Different dissolution profiles of each of the compartments can also give rise to delayed dissolution of selected components in the wash solution.

Compositions, Methods and Uses

As described in the above paragraphs, the present invention provides a liquid (dish wash detergent) composition comprising:
a) a strong sequestering builder,
b) a subtilisin, and
c) a subtilisin inhibitor which is a peptide aldehyde or a hydrosulfite adduct thereof or a peptide methyl ketone, wherein the methyl group is optionally halogen-substituted, and wherein the peptide optionally has an N-terminal protection group;
wherein the composition is essentially devoid of an anionic surfactant.

In an embodiment, the composition has a content of non-ionic surfactant below 5% by weight.

In an embodiment, the composition comprises the strong sequestering builder in an amount above 0.1% by weight.

In an embodiment, the strong sequestering builder is a phosphorus-containing builder. Preferably, the composition comprises the phosphorus-containing builder in an amount corresponding to a phosphorus content of at least 0.1% by weight of the composition, particularly above 1%, above 2%, above 3%, above 4% or above 5% by weight.

In an embodiment, the composition further comprises an additional enzyme selected from the group consisting of a lipase, a cutinase, an amylase, a carbohydrase, a cellulase, a pectinase, a pectate lyase, a mannanase, an arabinase, a galactanase, a xylanase, an oxidase, a perhydrolase, a laccase, a peroxidase, and a haloperoxidase. Preferably, the additional enzyme is an amylase.

In an embodiment, the inhibitor of the composition is an aldehyde or ketone having the formula P-(A)$_y$-L-(B)$_x$—B$^0$—R* or a hydrosulfite adduct of such aldehyde, wherein:
a) R* is H (hydrogen), CH$_3$, CX$_3$, CHX$_2$, or CH$_2$X;
b) X is a halogen atom;
c) B$^0$ is a single amino acid residue with L- or D-configuration of the formula —NH—CH(R)—C(=O)—;
d) x is 1, 2 or 3;
e) B$_x$ is independently a single amino acid residue, each connected to the next B or to B$^0$ via its C-terminal;
f) L is absent or independently a linker group of the formula —C(=O)—, —C(=O)—C(=O)—, —C(=S)—, —C(=S)—C(=S)— or —C(=S)—C(=O)—;
g) A is absent if L is absent or is independently a single amino acid residue connected to L via the N-terminal of the amino acid;
h) P is selected from the group consisting of hydrogen or if L is absent an N-terminal protection group;

i) y is 0, 1, or 2,
j) R is independently selected from the group consisting of $C_{1-6}$ alkyl, $C_{6-10}$ aryl or $C_{7-10}$ arylalkyl optionally substituted with one or more, identical or different, substituent's R';
k) R' is independently selected from the group consisting of halogen, —OH, —OR", —SH, —SR", —NH$_2$, —NHR", —NR"$_2$, —CO$_2$H, —CONH$_2$, —CONHR", —CONR"$_2$, —NHC(=N)NH$_2$; and
l) R" is a $C_{1-6}$ alkyl group.
m) x may be 1, 2 or 3.

Preferably, the inhibitor is an aldehyde having the formula P—B$^2$—B$^1$—B$^0$—H or an adduct having the formula P—B$^2$—B$^1$—N(H)—CHR—CHOH—SO$_3$M, wherein
a) H is hydrogen;
b) B$^0$ is a single amino acid residue with L- or D-configuration of the formula —NH—CH(R)—C(=O)—;
c) B$^1$ and B$^2$ are independently single amino acid residues;
d) R is independently selected from the group consisting of $C_{1-6}$ alkyl, $C_{6-10}$ aryl or $C_{7-10}$ arylalkyl optionally substituted with one or more, identical or different, substituent's R';
e) R' is independently selected from the group consisting of halogen, —OH, —OR", —SH, —SR", —NH$_2$, —NHR", —NR"$_2$, —CO$_2$H, —CONH$_2$, —CONHR", —CONR"$_2$, —NHC(=N)NH$_2$;
f) R" is a $C_{1-6}$ alkyl group; and
g) P is an N-terminal protection group.

In an embodiment, R is such that B$^0$=—NH—CH(R)—C(=O)— is Phe, Tyr or Leu.

In an embodiment, B$^1$ is Ala, Gly or Val.

In an embodiment, B$^2$ is Arg, Phe, Tyr or Trp.

In an embodiment, x=2, L is absent, A is absent, and P is p-methoxycarbonyl (Moc) or benzyloxycarbonyl (Cbz).

In an embodiment, the inhibitor of the composition is Cbz-Arg-Ala-Tyr-H, Ac-Gly-Ala-Tyr-H, Cbz-Gly-Ala-Tyr-H, Cbz-Gly-Ala-Tyr-CF$_3$, Cbz-Gly-Ala-Leu-H, Cbz-Val-Ala-Leu-H, Cbz-Val-Ala-Leu-CF$_3$, Moc-Val-Ala-Leu-CF$_3$, Cbz-Gly-Ala-Phe-H, Cbz-Gly-Ala-Phe-CF$_3$, Cbz-Gly-Ala-Val-H, Cbz-Gly-Gly-Tyr-H, Cbz-Gly-Gly-Phe-H, Cbz-Arg-Val-Tyr-H, Cbz-Leu-Val-Tyr-H, Ac-Leu-Gly-Ala-Tyr-H, Ac-Phe-Gly-Ala-Tyr-H, Ac-Tyr-Gly-Ala-Tyr-H, Ac-Phe-Gly-Ala-Leu-H, Ac-Phe-Gly-Ala-Phe-H, Ac-Phe-Gly-Val-Tyr-H, Ac-Phe-Gly-Ala-Met-H, Ac-Trp-Leu-Val-Tyr-H, MeO—CO-Val-Ala-Leu-H, MeNCO-Val-Ala-Leu-H, MeO—CO-Phe-Gly-Ala-Leu-H, MeO—CO-Phe-Gly-Ala-Phe-H, MeSO$_2$-Phe-Gly-Ala-Leu-H, MeSO$_2$—Val-Ala-Leu-H, PhCH$_2$O—P(OH)(O)-Val-Ala-Leu-H, EtSO$_2$-Phe-Gly-Ala-Leu-H, PhCH$_2$SO$_2$—Val-Ala-Leu-H, PhCH$_2$O—P(OH)(O)-Leu-Ala-Leu-H, PhCH$_2$O—P(OH)(O)-Phe-Ala-Leu-H, or MeO—P(OH)(O)-Leu-Gly-Ala-Leu-H or a hydrosulfite adduct of any of these, wherein Cbz is benzyloxycarbonyl and Moc is methoxycarbonyl. Preferably, the inhibitor is Cbz-Gly-Ala-Tyr-H or Moc-Val-Ala-Leu-H, or a hydrosulfite adduct thereof, wherein Cbz is benzyloxycarbonyl and Moc is methoxycarbonyl. Most preferably, the inhibitor is Cbz-Gly-Ala-Tyr-H, or a hydrosulfite adduct thereof, wherein Cbz is benzyloxycarbonyl.

In an embodiment, the strong builder of the composition is a tripolyphosphate, ethylene diamine tetraacetate, an organic phosphonate or a pyrophosphate, particularly as an alkali metal salt.

In an embodiment, the inhibitor and the subtilisin of the composition are present at a molar ratio of at least 1:1.

In an embodiment, the subtilisin of the composition has an amino acid sequence, which has at least 80% sequence identity, preferably at least 85%, at least 90%, at least 95%, at least 96%, at least 97%, at least 98%, or at least 99% sequence identity to SEQ ID NO: 1.

In an embodiment, the subtilisin of the composition has an amino acid sequence, which has at least 80% sequence identity, preferably at least 85%, at least 90%, at least 95%, at least 96%, at least 97%, at least 98%, or at least 99% sequence identity to SEQ ID NO: 4.

In yet another embodiment, the subtilisin of the composition has up to 10 amino acid changes, up to 9, up to 8, up to 7, up to 6, up to 5, up to 4, up to 3, up to 2, or up to 1 amino acid change(s) as compared to SEQ ID NO: 1 or SEQ ID NO: 4.

In another aspect, the invention also provides a method for stabilizing a subtilisin in a liquid (dish wash detergent) composition comprising mixing the ingredients of the liquid composition described above.

The invention also provides for use of the compositions and methods above for improving the storage stability of the subtilisin, and/or the storage stability of another additional enzyme included in the liquid composition. The additional enzyme is described above in the paragraph "Optional additional enzyme". The subtilisin activity is reduced by the inhibitor, and therefore the proteolytic degradation of other additional enzymes is reduced, and the storage stability is improved.

The pH of the liquid composition may be in the range 6.0-11; particularly in the range 6.0-10; particularly between 6.5-9.5; or between 7-9. pH may be measured directly in the composition or in a 5% solution in water.

EXAMPLES

Chemicals used as buffers and substrates were commercial products of at least reagent grade. Protease1, Protease2, Protease3, and Protease4, as used in the examples below, are subtilisin proteases. Protease1 has the amino acid sequence shown in SEQ ID NO: 1 (subtilisin 309). Protease2 has the amino acid sequence shown in SEQ ID NO: 2 (variant of subtilisin 309). Protease3 has the amino acid sequence shown in SEQ ID NO: 3 (variant of subtilisin 309). Protease4 has the amino acid sequence shown in SEQ ID NO: 4 (subtilisin BPN').

Example 1

A peptide aldehyde hydrosulfite adduct, XB$^1$—NH—CHR—CHOH—SO$_3$Na, was produced with a purity >80%, where X=Cbz-Gly; B$^1$=Ala; R=—CH$_2$-p(C$_6$H$_4$)—OH. This is the hydrosulfite adduct of Cbz-Gly-Ala-Tyr-H.

The peptide aldehyde hydrosulfite adduct described above was dissolved in 40% propylene glycol and water was added to make a 24% w/w solution of the adduct. Three different model liquid dishwashing detergents were prepared for testing the peptide aldehyde derived inhibitor representing three different levels of strong sequestering builder.

TABLE 2

Liquid detergent compositions.

| Component | Detergent A<br>% w/w<br>(invention) | Detergent B<br>% w/w<br>(invention) | Detergent C<br>% w/w<br>(reference) |
|---|---|---|---|
| Sodium tripolyphosphate | 20 | 0 | 0 |
| Tetrasodium pyrophosphate | 4 | 0 | 0 |
| Sodium carbonate | 2 | 7 | 7 |
| Etidronic acid (HEDP) | 0 | 1 | 0 |
| Sodium bicarbonate | 0 | 13 | 13 |

TABLE 2-continued

Liquid detergent compositions.

| Component | Detergent A % w/w (invention) | Detergent B % w/w (invention) | Detergent C % w/w (reference) |
|---|---|---|---|
| Sodium Citrate | 0 | 14 | 14 |
| Non-ionic surfactant (Pluronic PE 6800) | 1 | 0 | 0 |
| Xanthan gum | 2 | 2 | 2 |
| De-ionized water | ad 100% | ad 100% | ad 100% |
| pH adjusted to 8.0 with HCl | pH = 8.0 | pH = 8.0 | pH = 8.0 |
| Strong sequestering builder | yes | yes | no |
| Calculated phosphorus content | 5.9% | 0.3% | 0% |

The phosphorus content (P-content) is calculated by standard theoretical method, e.g. for detergent B with Etidronic acid (HEDP) as the only phosphoris containing component:

$$P_{content} = \frac{N_P * Mw_P}{Mw_{Etidroninc\ acid}} * \%\ w/w_{detergent} = \frac{2 * \frac{30.97\ g}{mol}}{206.028 \frac{g}{mol}} * 1\% = 0.3\%$$

To the detergent bases, the following amount of enzyme and inhibitor (peptide aldehyde hydrosulfite adduct described above) were added, all samples normalized to 100 g of detergent. Inhibitor amount in mg is given as the pure component (added from the 24% solution). Protease2 and Protease3 were used in concentrations of 0.04 g active enzyme protein per gram of enzyme solution. The mole ratio expresses the molar ratio of the inhibitor relative to the enzyme.

TABLE 3

| Detergent | Enzyme solution | Peptide aldehyde hydrosulfite adduct | Mole ratio |
|---|---|---|---|
| 98 g Detergent A | 2 g Protease3 | 0 | 0 |
| 98 g Detergent A | 2 g Protease3 | 3.4 mg | 2.1 |
| 98 g Detergent A | 2 g Protease2 | 0 | 0 |
| 98 g Detergent A | 2 g Protease2 | 3.4 mg | 2.1 |
| 98 g Detergent B | 2 g Protease3 | 0 | 0 |
| 98 g Detergent B | 2 g Protease3 | 3.4 mg | 2.1 |
| 98 g Detergent B | 2 g Protease2 | 0 | 0 |
| 98 g Detergent B | 2 g Protease2 | 3.4 mg | 2.1 |
| 98 g Detergent C | 2 g Protease3 | 0 | 0 |
| 98 g Detergent C | 2 g Protease3 | 3.4 mg | 2.1 |
| 98 g Detergent C | 2 g Protease2 | 0 | 0 |
| 98 g Detergent C | 2 g Protease2 | 3.4 mg | 2.1 |

The detergents were placed in closed glasses at 37° C. for 2 weeks. Residual activity of protease was measured (by comparison to a reference stored at −18° C.) using standard enzyme analytical method (protease activity measured by hydrolysis of N,N-dimethylcasein at 40° C., pH=8.3).

TABLE 4

| Residual protease activity after two weeks at 37° C. | Detergent A (invention) | Detergent B (invention) | Detergent C (reference) |
|---|---|---|---|
| Protease3, no inhibitor | 6% | 44% | 74% |
| Protease3, inhibitor | ≥100% | 92% | 85% |
| Protease2, no inhibitor | 1% | 10% | 76% |
| Protease2, inhibitor | 90% | ≥100% | ≥100% |

The results demonstrate that increasing amounts of strong sequestering builder tend to destabilize the subtilisin, and that the peptide aldehyde hydrosulfite adduct is particularly effective to stabilize the subtilisin in liquid formulations which include phosphorus-containing builder salts.

Example 2

Various peptide aldehydes were produced, all with a purity >80%. The peptide aldehydes were dissolved in DMSO to a concentration of 10 mg/ml before use.

To detergent A from Example 1, the following amount of enzyme and different inhibitors (peptide aldehydes) were added, all samples normalized to 100 g of detergent. Inhibitor amount in mg is given as the pure component (added from the 10 mg/mL solution). Three subtilisin proteases were used: Protease1, Protease2, and Protease4, all in concentration of 0.04 g active enzyme protein per gram of enzyme solution.

TABLE 5

| Detergent | Enzyme solution | Peptide aldehyde | Mole ratio |
|---|---|---|---|
| 98 g Detergent A | 2 g Protease4 | 0 | 0 |
| 98 g Detergent A | 2 g Protease4 | 3.3 mg Moc-VAL-H | 3.2 |
| 98 g Detergent A | 2 g Protease1 | 0 | 0 |
| 98 g Detergent A | 2 g Protease1 | 3.3 mg Cbz-GAY-H | 2.6 |
| 98 g Detergent A | 2 g Protease2 | 0 | 0 |
| 98 g Detergent A | 2 g Protease2 | 3.3 mg Cbz-GAY-H | 2.6 |

The detergents were placed in closed glasses at 37° C. for 2 weeks. Residual activity of protease was measured (by comparison to a reference stored at −18° C.) using standard enzyme analytical method (protease activity measured by hydrolysis of N,N-dimethylcasein at 40° C., pH=8.3).

TABLE 6

|  | Residual protease activity after two weeks at 37° C. |
|---|---|
| Protease4, no inhibitor | 5% |
| Protease4, Moc-Val-Ala-Leu-H | 57% |
| Protease1, no inhibitor | 25% |
| Protease1, Cbz-Gly-Ala-Tyr-H | 81% |
| Protease2, no inhibitor | 1% |
| Protease2, Cbz-Gly-Ala-Tyr-H | 86% |

The results demonstrate that peptide aldehydes are effective to stabilize subtilisins in liquid formulations which include a strong sequestering builder.

The invention claimed is:

1. A liquid automatic dish wash detergent composition comprising:
   a) a strong sequestering builder;
   b) a subtilisin; and
   c) a subtilisin inhibitor which is a peptide aldehyde or a hydrosulfite adduct thereof or a peptide methyl ketone, wherein the methyl group is optionally halogen-substituted, and wherein the peptide optionally has an N-terminal protection group;
wherein the composition comprises a surfactant but is devoid of an anionic surfactant.

2. The composition of claim 1, wherein the surfactant is a non-ionic surfactant present in an amount below 5% by weight of the composition.

3. The composition of claim 1, which comprises the strong sequestering builder in an amount above 0.1% by weight.

4. The composition of claim 1, wherein the strong sequestering builder is a phosphorus-containing builder.

5. The composition claim 4, which comprises the phosphorus-containing builder in an amount corresponding to a phosphorus content of at least 0.1% by weight of the composition.

6. The composition of claim 1, which further comprises an additional detergent enzyme.

7. The composition of claim 1, wherein the inhibitor is an aldehyde or ketone having the formula P-(A)$_y$-L-(B)$_x$—B$^0$—R* or a hydrosulfite adduct of such aldehyde, wherein:
   a) R* is H (hydrogen), CH$_3$, CX$_3$, CHX$_2$, or CH$_2$X;
   b) X is a halogen atom;
   c) B$^0$ is a single amino acid residue with L- or D-configuration of the formula NH—CH(R)—C(=O)—;
   d) x is 1, 2 or 3;
   e) B$_x$ is independently a single amino acid residue, each connected to the next B or to B$^0$ via its C-terminal;
   f) L is absent or independently a linker group of the formula —C(=O)—, —C(=O)—C(=O)—, —C(=S)—, —C(=S)—C(=S)— or —C(=S)—C(=O)—;
   g) A is absent if L is absent or is independently a single amino acid residue connected to L via the N-terminal of the amino acid;
   h) P is selected from the group consisting of hydrogen or if L is absent an N-terminal protection group;
   i) y is 0, 1, or 2;
   j) R is independently selected from the group consisting of C$_{1-6}$ alkyl, C$_{6-10}$ aryl or C$_{7-10}$ arylalkyl optionally substituted with one or more, identical or different, substituent's R';
   k) R' is independently selected from the group consisting of halogen, —OH, —OR", —SH, —SR", —NH$_2$, —NHR", —NR"$_2$, —CO$_2$H, —CONH$_2$, —CONHR", —CONR"$_2$, —NHC(=N)NH$_2$; and
   l) R" is a C$_{1-6}$ alkyl group.

8. The composition of claim 7 wherein R is such that B$^0$=—NH—CH(R)—C(=O)— is Phe, Tyr or Leu.

9. The composition of claim 7, wherein x=2, L is absent, A is absent, and P is p-methoxycarbonyl (Moc) or benzyloxycarbonyl (Cbz).

10. The composition of claim 1, wherein the inhibitor is an aldehyde having the formula P—B$^2$—B$^1$—B$^0$—H or an adduct having the formula P—B$^2$—B$^1$—N(H)—CHR—CHOH—SO$_3$M, wherein
    a) H is hydrogen;
    b) B$^0$ is a single amino acid residue with L- or D-configuration of the formula —NH—CH(R)—C(=O)—;
    c) B$^1$ and B$^2$ are independently single amino acid residues;
    d) R is independently selected from the group consisting of C$_{1-6}$ alkyl, C$_{6-10}$ aryl or C$_{7-10}$ arylalkyl optionally substituted with one or more, identical or different, substituent's R';
    e) R' is independently selected from the group consisting of halogen, —OH, —OR", —SH, —SR", —NH$_2$, —NHR", —NR"$_2$, —CO$_2$H, —CONH$_2$, —CONHR", —CONR"$_2$, —NHC(=N)NH$_2$;
    f) R" is a C$_{1-6}$ alkyl group; and
    g) P is an N-terminal protection group.

11. The composition of claim 10, wherein B$^1$ is Ala, Gly or Val.

12. The composition of claim 10, wherein B$^2$ is Arg, Phe, Tyr or Trp.

13. The composition of claim 10, wherein R is such that B$^0$=—NH—CH(R)—C(=O)— is Phe, Tyr or Leu.

14. The composition of claim 1, wherein the inhibitor is Cbz-Arg-Ala-Tyr-H, Ac-Gly-Ala-Tyr-H, Cbz-Gly-Ala-Tyr-H, Cbz-Gly-Ala-Tyr-CF$_3$, Cbz-Gly-Ala-Leu-H, Cbz-Val-Ala-Leu-H, Cbz-Val-Ala-Leu-CF$_3$, Moc-Val-Ala-Leu-CF$_3$, Cbz-Gly-Ala-Phe-H, Cbz-Gly-Ala-Phe-CF$_3$, Cbz-Gly-Ala-Val-H, Cbz-Gly-Gly-Tyr-H, Cbz-Gly-Gly-Phe-H, Cbz-Arg-Val-Tyr-H, Cbz-Leu-Val-Tyr-H, Ac-Leu-Gly-Ala-Tyr-H, Ac-Phe-Gly-Ala-Tyr-H, Ac-Tyr-Gly-Ala-Tyr-H, Ac-Phe-Gly-Ala-Leu-H, Ac-Phe-Gly-Ala-Phe-H, Ac-Phe-Gly-Val-Tyr-H, Ac-Phe-Gly-Ala-Met-H, Ac-Trp-Leu-Val-Tyr-H, MeO—CO-Val-Ala-Leu-H, MeNCO-Val-Ala-Leu-H, MeO—CO-Phe-Gly-Ala-Leu-H, MeO—CO-Phe-Gly-Ala-Phe-H, MeSO$_2$-Phe-Gly-Ala-Leu-H, MeSO$_2$-Val-Ala-Leu-H, PhCH$_2$O—P(OH)(O)-Val-Ala-Leu-H, EtSO$_2$-Phe-Gly-Ala-Leu-H, PhCH$_2$SO$_2$-Val-Ala-Leu-H, PhCH$_2$O—P(OH)(O)-Leu-Ala-Leu-H, PhCH$_2$O—P(OH)(O)-Phe-Ala-Leu-H, or MeO—P(OH)(O)-Leu-Gly-Ala-Leu-H or a hydrosulfite adduct of any of these, wherein Cbz is benzyloxycarbonyl and Moc is methoxycarbonyl.

15. The composition of claim 1, wherein the inhibitor is Cbz-Gly-Ala-Tyr-H or Moc-Val-Ala-Leu-H, or a hydrosulfite adduct thereof, wherein Cbz is benzyloxycarbonyl and Moc is methoxycarbonyl.

16. The composition of claim 1, wherein the strong builder is a tripolyphosphate, ethylene diamine tetraacetate, an organic phosphonate or a pyrophosphate, particularly as an alkali metal salt.

17. The composition of claim 1, wherein the inhibitor and the subtilisin are present at a molar ratio of at least 1:1.

18. The composition of claim 1, wherein the subtilisin has an amino acid sequence, which has at least 80% sequence identity to SEQ ID NO: 1 or SEQ ID NO: 4, or which has up to 10 amino acid changes as compared to SEQ ID NO: 1 or SEQ ID NO: 4.

19. The composition of claim 1, wherein the strong sequestering builder is a non-phosphorus-containing builder.

20. The composition of claim 1, wherein the strong sequestering builder is selected from the group consisting of ethylenediaminetetraacetic acid (EDTA), methylglycinediacetic acid (MGDA), Nitrilotriacetic acid (NTA), iminodisuccinic acid (IDS), ethylenediaminedisuccinic acid (EDDS), L-glutamic acid N,N-diacetic acid tetra sodium salt (GLDA) and a combination thereof.

* * * * *